United States Patent [19]

Lukacs

[11] Patent Number: 4,772,274
[45] Date of Patent: Sep. 20, 1988

[54] VAGINAL CLEANING APPARATUS

[76] Inventor: Stephen J. Lukacs, 12104 Pepperdine Pl., Orlando, Fla. 32826

[21] Appl. No.: 37,168

[22] Filed: Apr. 10, 1987

[51] Int. Cl.$^4$ ............................................. A61M 31/00
[52] U.S. Cl. ..................................... 604/275; 604/279
[58] Field of Search ............... 604/279, 207, 208, 209, 604/210, 220, 275, 264

[56] References Cited

U.S. PATENT DOCUMENTS

| | | | |
|---|---|---|---|
| 2,869,541 | 1/1959 | Helmer et al. | 604/210 |
| 3,577,980 | 5/1971 | Cohen | 604/220 X |
| 3,731,682 | 5/1973 | Fielding | 604/275 |
| 4,309,995 | 1/1982 | Sacco | 604/279 X |

FOREIGN PATENT DOCUMENTS 20836 of 1909 United Kingdom ................ 604/279

*Primary Examiner*—John D. Yasko
*Attorney, Agent, or Firm*—James H. Beusse

[57] ABSTRACT

A vaginal cleaning apparatus for cosmetic purposes which overcomes the disadvantages of commercially available douches. The apparatus comprises a solution chamber incorporating a plunger for expelling substantially all solution contained in the chamber through an attached cannula. A sponge applicator is attached to one end of the chamber surrounding the cannula. The cannula is in the form of a tube having a single opening for discharge of solution at its tip. The sponge applicator has an expanded shape approximately the inner configuration of a vagina. The sponge applicator is initially compressed for ease of insertion and expands from its tip as the solution is discharged. The chamber volume and application absorption are preferably matched to minimize dripping of the solution. The cannula and applicator extend at an angle with respect to the chamber to allow use of the apparatus in a standing or sitting position.

4 Claims, 2 Drawing Sheets

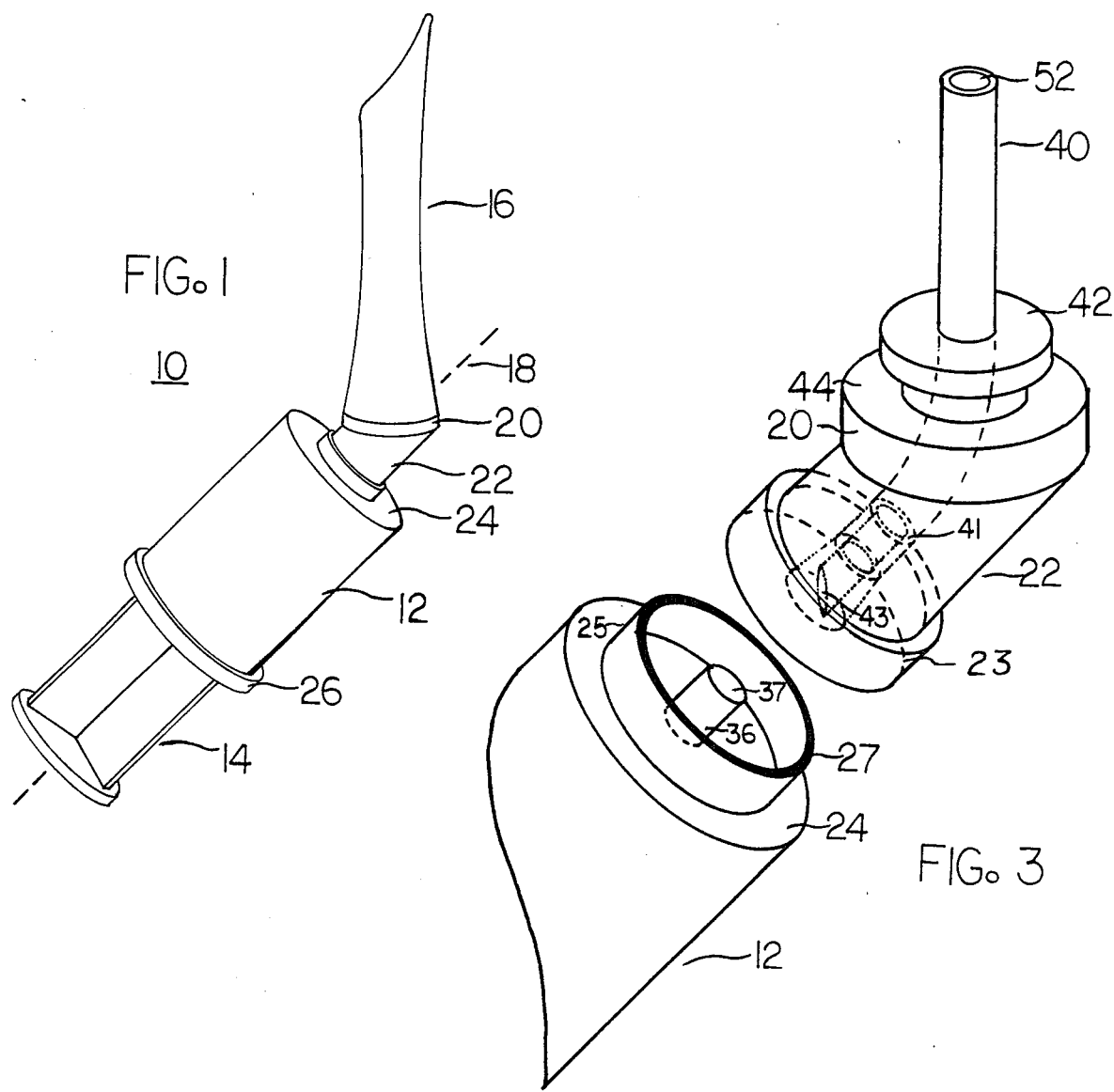
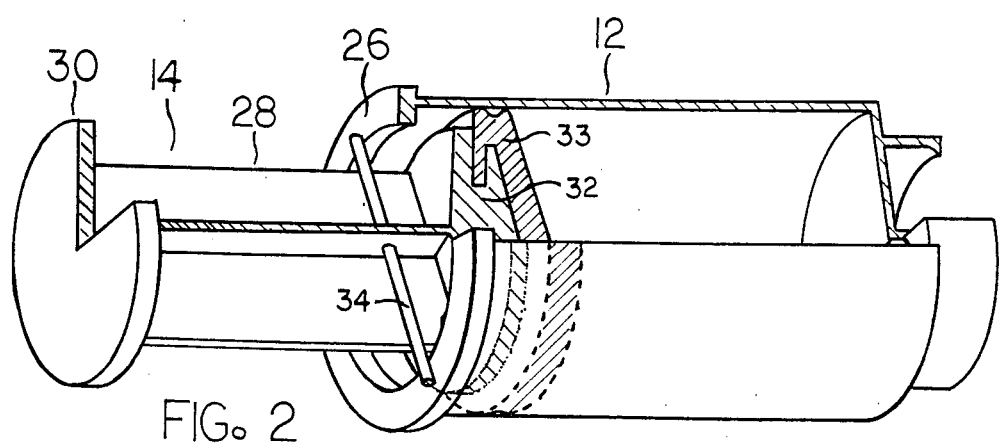

VAGINAL CLEANING APPARATUS

This invention relates to feminine hygiene and, more particularly, to portable, disposable vaginal cleaning apparatus.

The increasing emphasis on feminine hygiene has led to the growth of a rather large industry directed to the production of portable, disposable single use douches. Such products are available under the names of "Feminique" TM of Ennis Laboratories, Edison, N.J.; "Massengill" TM of Beecham Products, Pittsburgh, Pa.; "Summer's Eve" TM of C.B. Fleet Company, Inc., Lynchburg, Va. All of these devices provide a premeasured portion of a cleansing and rinsing solution which is utilized to wash the interior of the vagina primarily for the purpose of reducing body odor. In general, all of these devices include a cannula attached to a squeeze bottle which is compressed to discharge liquid through openings in the cannula after insertion in the vagina.

A disadvantage of these prior art devices is that they must be used in a location which permits the liquid solution discharged from the douche to be readily collected as it is expelled. Furthermore, since the primary function of this type of douche is a rinsing operation, the solution tends to run back along the cannula and onto the squeeze bottle as the solution is being applied thus creating an unsanitary condition. Still further, because these douches utilize a squeeze bottle approach for applying pressure to expel solution, it is generally necessary that such devices be used in a reclining position. Still further, because the devices are generally designed to be portable, the volume of solution available in a single douche is relatively small and may not be sufficient to effect proper cleaning using such a rinsing technique. Additionally, a considerable portion of the solution is often not extractable from the douche.

SUMMARY OF THE INVENTION

It is an object of the present invention to provide a portable, disposable vaginal cleansing apparatus which overcomes the abovementioned disadvantages of presently available douches.

It is another object of the present invention to provide a vaginal cleaning apparatus which provides a cleaning function without generating an excess of solution.

It is a still further object of the present invention to provide a vaginal cleaning apparatus which can be utilized in any position and permits ready dispensing of solution.

In an exemplary embodiment, the present invention comprises an apparatus for vaginal cleaning including a syringe having an elongated solution chamber with openings at opposite ends of the chamber. A plunger is inserted into one of the openings and is operable to expel solution through the other of the openings. A cannula is attached to the end of the chamber opposite the chamber and extends at an oblique angle with respect to a longitudinal axis through the chamber. The cannula is covered by a sponge applicator which has a central opening through which the cannula fits and has an external configuration, when expanded by moisture, approximating the shape and dimensions of a human vagina. The sponge applicator is preferably an open cell, skinless relatively soft material. In use, the sponge applicator is provided in a compressed configuration to facilitate insertion. As the plunger is depressed expelling the solution through the cannula, the sponge absorbs the solution from the chamber and begins to expand. In the preferred embodiment, the cannula has a single opening near its tip distal from the solution chamber so that the sponge begins to absorb solution at the tip end. The solution then trickles down towards the solution chamber and is absorbed by the remaining sponge material causing it to expand during absorption. Once the solution chamber has been completely emptied, all the solution is contained in the sponge such that the sliding friction associated with removing the sponge covered cannula acts as a scrubbing action to effect a more efficient cleaning and removal of bacteria creating odor from the vaginal cavity.

DESCRIPTION OF THE DRAWINGS

For a better understanding of the present invention, reference may be had to the following detailed description taken in conjunction with the accompanying drawing in which:

FIG. 1 is a perspective view of a preferred form of the present invention;

FIG. 2 is a partial cutaway perspective view of the solution chamber and plunger assembly for use with the invention shown in FIG. 1;

FIG. 3 is an exploded perspective view of the end of the solution chamber of FIG. 1 illustrating the oblique connection to the connection;

DETAILED DESCRIPTION

Figure 4:
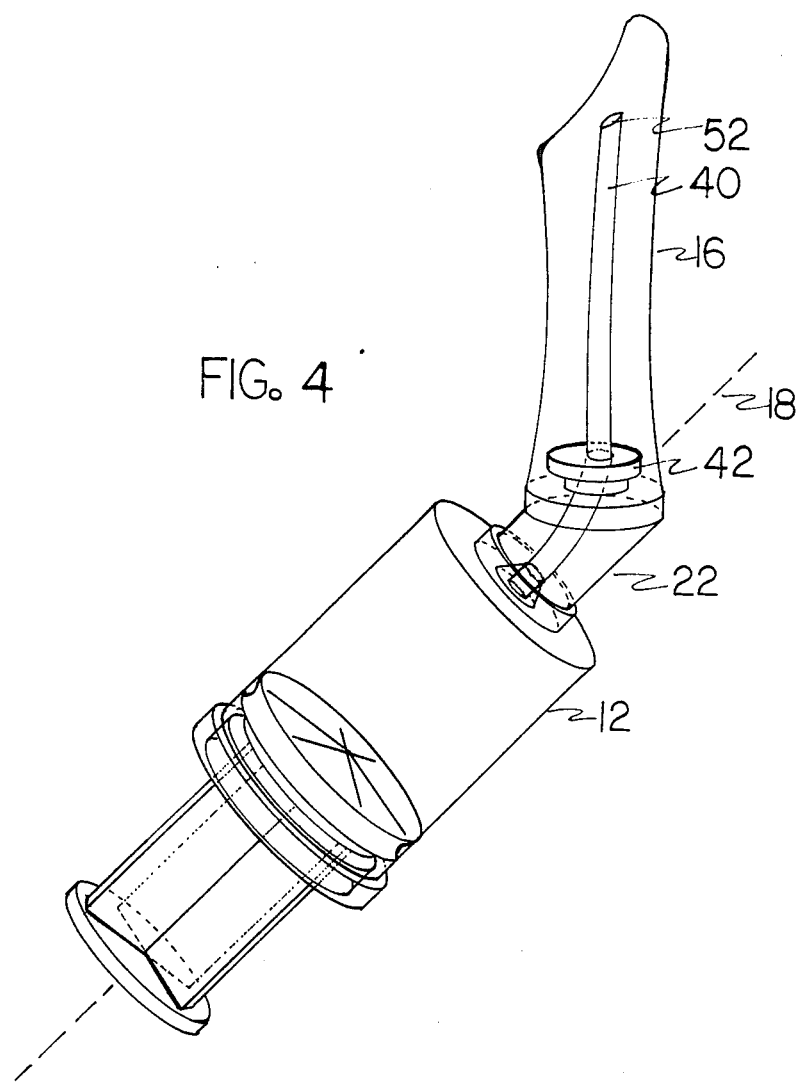
FIG. 4 is a perspective view of the solution container and assembled cannula with the sponge applicator shown in phantom.

Referring now to FIG. 1, there is shown a perspective view of one form of the present inventive feminine hygiene cleansing apparatus indicated generally at 10. The apparatus comprises a generally elongated solution chamber 12 having one end adapted to receive a plunger 14 and a second end for connection to a sponge applicator 16. The sponge applicator has an expanded shape as shown in FIG. 1 generally configured to an internal configuration of a vaginal cavity. The applicator extends at an angle oblique to a primary axis 18 through the solution chamber 12. The sponge applicator is attached to a locking base 20, which base is connected to a tubular extension or coupling 22 coupled between the sponge applicator and an end 24 of the solution chamber 12. The coupling 22 is attached to the end 24 of chamber 12 at one end and has a second end formed at a biased angle to create the oblique dependency of the sponge applicator 16. Preferably, the angle at which the applicator 16 extends with respect to the central axis 18 is between 30 and 45 degrees. It will also be noted that the solution chamber 12 has an annular ring 26 formed around the end of the chamber at which the plunger 14 is inserted. The ring 26, as will become apparent, performs a dual function of having an outside ridge extending radially from the solution chamber for ease of holding the solution chamber while pressing the plunger and also includes an inner ridge, shown in FIG. 2, which extends radially inward of the solution chamber for preventing the plunger 14 from being withdrawn from the chamber 12.

Turning now to FIG. 2, there is shown a partial cutaway perspective view of the solution chamber 12 toward the end in which the plunger 14 is inserted. The plunger 14 may comprise a cross shaped member 28 having an outer cap 30 connected thereto and an inner cap 32 positioned within the chamber 12. The inner cap 32 is covered with a rubber stopper 33 which fits snugly within the chamber 12 so that as the plunger 14 is depressed, the rubber stopper serves to expel solution from the opposite end of the chamber 12. The ring 26 can be seen to extend both radially outward and radially inward of the walls of chamber 12. Since the cap 32 has a larger diameter than the inner diameter of the ring 26, the plunger 14 cannot be removed from the solution chamber 12. While this feature is useful in preventing solution from being removed from the chamber by accidental extraction of the plunger 14, the feature is also a safety feature which prevents refilling of the chamber once the unit has been used. For additional protection during transportation of the apparatus 10, there is provided a rod 34 extending through one of the arms of the cross shape member 28 and having ends resting on an outer surface of the ring 26. Preferably, the rod 34 is a frangible, plastic material which is easily broken by a reasonable amount of pressure exerted on the plunger 14. The rod 34 prevents the plunger 14 from being accidentally depressed.

By reference to FIG. 3, there can be seen one arrangement for connecting the sponge applicator 16 to an end of the solution chamber 12. In this embodiment, the coupling 22 is seen to be a short cylindrical coupling member, preferably formed of plastic, as is the solution chamber 12, and having an enlarged portion 23 forming a ridge-like circumferential connector at an end of the coupling. A mating circular connector 25 extends from the end 24 of chamber 12 for receiving the portion 23. The connector 25 may have a radially inward extending lip 27 for effecting a locking action when portion 23 is slid or snapped into connector 25. A tube 36 is attached to the solution chamber 12 and projects upward centrally through the connector 25. The tube 36 has approximatley the same height above surface or end 24 as the connector 25. The tube 36 may be formed as a part of chamber 12 such as by injection molding. The exposed end of tube 36 is preferably covered by a thin plastic or other type film 37 for containing the liquid solution in chamber 12. As previously noted, the coupling 22 is formed with a bias at one end such as, for example, a 45 degree angle, so that the base 20 attached to the bias cut coupling 22 extends at an angle of between 30 and 45 degrees with respect to the central axis 18 passing through the chamber 12 in the direction in which the plunger 14 is depressed. A cannula 40 extends through coupling 22 and attaches to a tube support 41. The support 41 includes an inner tube connector 43 adapted for mating with tube 36. Tube connector 43 is formed with a bias cut end to permit ready penetration of the film 37 covering tube 36.

The cannula 40 passes through and at least frictionally engages base member 20. The base member 20 includes an upper circular plate 42 spaced above a surface 44 but attached to the base 20. The plate 42 fits within an annular groove formed internally of the sponge applicator 16 adjacent its lower edge for holding the applicator firmly to the base 20.

FIG. 4 is a more detailed showing of the assembled sponge applicator 16, cannula 40 and solution chamber 12 with the elements being transparent in order to illustrate the interconnection of the various elements. As can be seen, the sponge applicator 16 has a central bore within which the cannula 40 extends. Near the base of the applicator 16 there is provided an annular slot into which the plate 42 fits and serves to hold the sponge applicator 16 into position over the cannula 40. While not shown, the portion 23 and connector 25 could include mating interlocking groove and protrusions, respectively, for attaching the two units together in a manner to prevent rotation. Furthermore, while the assembly has been shown as being constructed with the coupling and cannula assembly formed as a single unit and the base attachment point being at the surface 24 of the solution chamber 12, the apparatus may as easily comprise a coupling extending from the solution chamber 12 with a connection between the coupling and cannula being arranged to create the extension of the sponge applicator at an angle with respect to the solution chamber. In either arrangement, it is desirable that the connection to chamber 12 be external thereof such that all of the solution in chamber 12 can be expelled by depression of plunger 14. Furthermore, it is possible to use a removable cap to protect tube 36 and thus to avoid the requirement to puncture a plastic film in order to connect the cannula 40 to chamber 12.

Figures 5A, 5B, 5C, 5D:
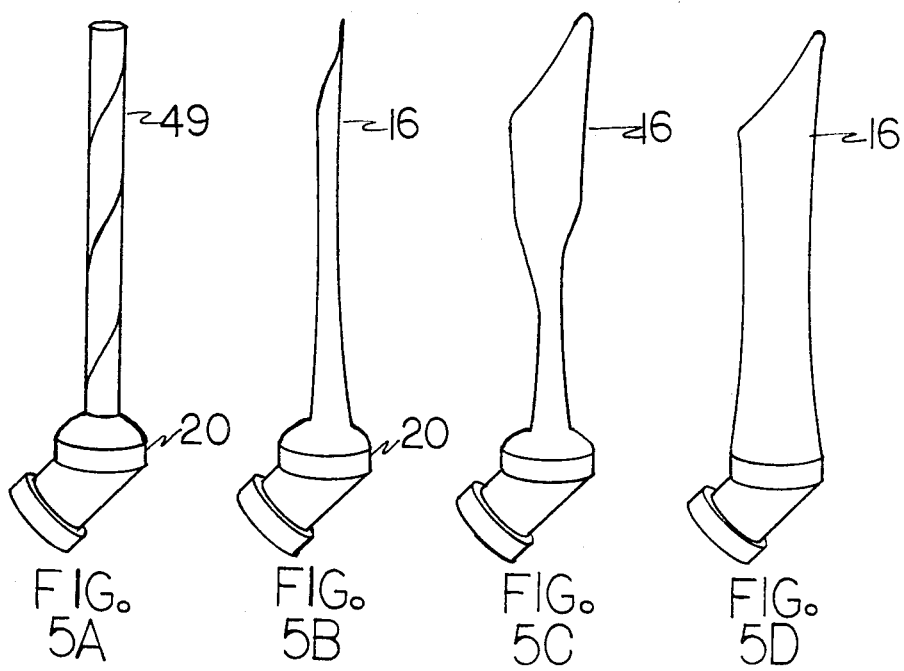
FIGS. 5A through 5D illustrate the compressed state of the sponge applicator and succeeding stages of expansion.

In the use of the apparatus 10, the sponge applicator is attached to the solution chamber 12 while the sponge applicator is in a dry compressed state. Referring to FIG. 5A, there is shown a compressed form of a sponge applicator 16, at the time of initial attachment to the solution chamber 12, with a constricting covering 49 in place. FIG. 5B shows the form at time of insertion before any solution has been expelled. This compressed form is sufficiently small to allow relatively easy insertion into a vaginal cavity. Once inserted, depression of the plunger 14 causes the solution from chamber 12 to be expelled through the distal end 52 (see FIG. 3) of cannula 40. As a result, the distal end of the sponge applicator 16 begins to expand as the fluid enters the sponge material as shown in FIG. 5C. As the solution continues to be expelled into and collected by the sponge material, the entire sponge applicator 16 assumes the shape as shown in FIG. 5D. At this time, withdrawal of the sponge applicator results in a scrub type of cleaning action of the vaginal walls greatly enhancing the ability of the cleaning solution to remove odor causing bacteria and/or bodily excretions contributing to odor. The compressed form shown in FIG. 5A may be achieved by packaging of the applicator in a cardboard tube or other suitable wrapping during the dry state. The sponge material may be a synthetic material of the type generally described as open cell with relatively small air spales. It should be formed skinless and be relatively soft with high teaking resistance and ability to absorb polar solutions. High resilience is necessary for expansion.

The oblique angle at which the sponge applicator extends with regard to the solution chamber 12 enhances the ability of the unit to be utilized without creating undue discomfort and unsanitary handling of the apparatus. Furthermore, the oblique angle allows insertion of the sponge applicator in various positions including sitting and standing. Still further, since the sponge 16 serves to absorb all of the solution from the chamber 12, there is not requirement for a basin or other chamber to collect liquid normally associated with a douching action. Thus, the present invention provides a more sanitary method of vaginal cleaning and greatly enhances the ability of a person to utilize the apparatus without the disadvantages associated with ordinary douche type cleaning.

While the invention has been described in what is presently considered to be a preferred embodiment, other forms will be apparent to those having ordinary skill in the art. It is intended, therefore, that the invention not be limited to the disclosed embodiment but that it be interpreted within the spirit of the appended claims.

I claim:

1. Apparatus for vaginal cleaning comprising:

a syringe having an elongated solution chamber with openings at opposite ends thereof, a plunger inserted into one of the openings and operable to expel solution through another of the openings;

a cannula having one end connected to said syringe at an oblique angle with respect to a longitudinal axis thereof, said one end including connection means for attaching said cannula to said syringe when said one end is inserted into said another of the openings in said syringe, said cannula extending obliquely with respect to a primary axis of said syringe;

a sponge applicator dimensioned to fit over and envelop said cannula, said applicator having a substantially central opening for receiving said cannula and having an external configuration when wet approximating a configuration of a human vagina, said applicator including means attaching it to said cannula; and means for interlocking such sponge applicator to such solution chamber comprising a tubular coupling extending from an end of said chamber, the coupling including a base member having a spaced circular plate attached thereto, the sponge applicator having a bottom opening with an internal annular groove positioned and dimensioned to fit over and encompass at least an outer circumferential portion of the plate for interlocking the applicator to the chamber.

2. The apparatus of claim 1 wherein said syringe is dimensioned to contain a volume of solution approximately equal to the solution absorption capacity of said sponge applicator whereby all of the solution is absorbed by said applicator.

3. A vaginal cleaning apparatus for effecting a scrubbing action for feminine hygiene comprising a syringe including a solution chamber for holding a cleaning solution and a plunger for forcibly expelling the solution, a cannula attached to said syringe at an oblique angle with respect to an axis of motion of the plunger, a sponge applicator attached to and enveloping said cannula, said sponge applicator having a compressed, relatively small radial cross-section when dry and being readily expandable when wet whereby said applicator may be easily inserted when dry and caused to expand by expelling solution from said cannula such that withdrawal of said applicator effects a scrubbing and cleaning action, said syringe being dimensioned to contain a volume of solution approximately equal to the solution absorption capacity of said sponge applicator whereby all of the solution is absorbed by said applicator, and means for interlocking said syringe to said solution chamber for preventing withdrawal of said cannula from said sponge when withdrawing said applicator during use.

4. A vaginal cleaning apparatus for effecting a scrubbing action for feminine hygiene comprising a syringe including a solution chamber for holding a cleaning solution and a plunger for forcibly expelling the solution, a cannula attached to said syringe at an oblique angle with respect to an axis of motion of the plunger, a sponge applicator attached to and enveloping said cannula, said sponge applicator having a compressed, relatively small radial cross-section when dry and being readily expandable when wet whereby said applicator may be easily inserted when dry and caused to expand by expelling solution from said cannula such that withdrawal of said applicator effects a scrubbing and cleaning action, said syringe being dimensioned to contain a volume of solution approximately equal to the solution absorption capacity of said sponge applicator whereby all of the solution is absorbed by said applicator, and means for interlocking said syringe to said solution chamber for preventing withdrawal of said cannula from said sponge when withdrawing said applicator during use, said interlocking means comprising a tubular coupling extending from an end of said chamber, the coupling including a base member having a spaced circular plate attached thereto, the sponge applicator having a bottom opening with an internal annular groove positioned and dimensioned to fit over and encompass at least an outer circumferential portion of the plate for interlocking the applicator to the chamber.

* * * * *

UNITED STATES PATENT AND TRADEMARK OFFICE
CERTIFICATE OF CORRECTION

PATENT NO. : 4,772,274
DATED : September 20, 1988
INVENTOR(S) : Stephen J. Lukacs, Jr.

It is certified that error appears in the above-identified patent and that said Letters Patent is hereby corrected as shown below:

On the first page, please indicate the inventor's name as "Stephen J. Lukacs, Jr."

Signed and Sealed this

Seventh Day of February, 1989

Attest:

DONALD J. QUIGG

*Attesting Officer*  *Commissioner of Patents and Trademarks*